United States Patent [19]

Song

[11] 4,303,539

[45] Dec. 1, 1981

[54] OIL ADDITIVES CONTAINING A THIOCARBAMYL MOIETY

[75] Inventor: Won R. Song, Short Hills, N.J.

[73] Assignee: Exxon Research & Engineering Co., Florham Park, N.J.

[21] Appl. No.: 218,446

[22] Filed: Dec. 19, 1980

Related U.S. Application Data

[63] Continuation of Ser. No. 74,821, Sep. 12, 1979, abandoned.

[51] Int. Cl.$^3$ .............................................. C10M 1/38
[52] U.S. Cl. ..................................... 252/47; 525/352; 564/17
[58] Field of Search ......................................... 252/47

[56] References Cited

U.S. PATENT DOCUMENTS

| | | | |
|---|---|---|---|
| 2,209,464 | 7/1940 | Loane et al. | 252/47 |
| 2,230,691 | 2/1941 | Lewis | 252/47 |
| 2,373,049 | 4/1945 | Pedersen | 252/47 X |
| 2,925,781 | 2/1960 | Fischer | 252/47 X |
| 3,047,501 | 7/1962 | Brook et al. | 252/47 X |
| 3,251,811 | 5/1966 | Warner et al. | 252/47 X |
| 3,296,136 | 1/1967 | Eickemeyer et al. | 252/47 X |
| 3,352,781 | 11/1967 | Buehler | 252/47 X |
| 3,822,209 | 7/1974 | Knapp et al. | 252/47 |

FOREIGN PATENT DOCUMENTS 1487576  7/1967  France ................................ 252/47

*Primary Examiner*—Andrew Metz
*Attorney, Agent, or Firm*—R. A. Dexter; J. J. Mahon

[57] ABSTRACT

Thiocarbamyl derivatives, including thioureas and thiocarbamic esters derived from the reaction of an alkenyl isothiocyanate with an amine and alcohol or thio, respectively, have utility as an additive for hydrocarbons, particularly fuels and mineral lubricating oils whereby enhanced anticorrosion, oxidation inhibition and/or dispersancy activity is imparted to said hydrocarbons.

2 Claims, No Drawings

OIL ADDITIVES CONTAINING A THIOCARBAMYL MOIETY

This is a continuation, of application Ser. No. 74,821, filed Sept. 12, 1979 and now abandoned.

BACKGROUND OF THE INVENTION

1. Field of the Invention

This invention relates to sulfur- and nitrogen-containing compositions and in a more particular sense it relates to those compounds having a thiocarbamyl moiety adapted for use as additives in hydrocarbon oils. This invention relates also to hydrocarbon oils, especially lubricating oil compositions containing said sulfur- and nitrogen-containing compositions.

2. General Background

The problem of deterioration of hydrocarbon oils has been the cause of principal concern in the formulation of hydrocarbon oil compositions such as fuels and lubricating compositions. Deterioration of hydrocarbon oils results in the formation of products which are corrosive to the metal surfaces with which the oils come into contact. It results also in the formation of products which have a tendency to agglomerate to form sludge and varnish-like deposits.

In recent years it has been a common practice to incorporate into hydrocarbon oils chemical additives which are capable of inhibiting the deterioration of oil and the formation of these harmful deposits. Such additives have generally been classified into three principal groups according to the manner in which they function to improve hydrocarbon oil. One group of such additives are the oxidation inhibitors which function to stabilize the oil against oxidative degradation. Another group of such additives are the corrosion inhibitors which counteract the corrosiveness of the products of oil degradation or passivate the metal surfaces against the corrosive action of such products. Still another group of such additives are the detergents or dispersing agents which function to maintain products of oil degradation in dispersion in the oil phase and to prevent the deposition of sludge and varnish.

Two or more such additives are often needed in a hydrocarbon oil to stabilize the oil against formation of harmful degradation products. The incorporation in an oil, however, of several different types of additives not only is costly, but is also dependent upon the compatibility of the additives with one another. Thus, it is known that additives which are effective separately may not be used in combination because of their incompatibility. A great deal of effort has recently been devoted to the development of so-called "multifunctional" additive, i.e., an additive which, by itself, is capable of imparting several desirable properties to an oil. It will be readily appreciated that the use of such additive is highly advantageous from the standpoint of both economy and convenience.

3. Prior Art Publications

Sulfur- and nitrogen-containing compositions are stated to provide such desirable multifunctional activity to both fuels and lubricating oils. For example, in U.S. Pat. No. 2,168,674 to Loane et al, mineral oils containing fatty acid thiocyanates, such as lauroyl thiocyanate and stearoyl thiocyanate, have been suggested as oxidation inhibitors for lubricating oils; in U.S. Pat. No. 2,169,700, the same inventors have disclosed mineral oils containing polythiocyanates having the formula, $R(SCN)_n$, wherein R is an aliphatic radical or an aromatic radical, and n is an integer greater than one; and, in U.S. Pat. Nos. 2,619,464 and 2,680,759 it is reported that mineral lubricating oils containing small amounts of high molecular weight alkyl monothiocyanates, preferably $C_{21}$–$C_{34}$ monothiocyanates as paraffin wax monothiocyanates, are resistant to oxidation and have a reduced tendency to corrode hard metal alloy bearings (the polythiocyanates are noted as ineffective due to their substantial insolubility in mineral lubricating oils). The referenced latter compositions are produced by the reaction of an alkyl chloride with an inorganic salt of thiocyanic acid, e.g. ammonium thiocyanate, at a temperature of at least 100° C.

U.S. Pat. No. 3,330,763 discloses the use of hydrocarbylamine salts of thiocyanic acid as load-carrying additives in lubricating oils.

Further, the isomerization of allylic thiocyanates has been attributed to the occurrence of a cyclic intromolecular transition state (Organic Sulfur Compounds edited by N. Kharasch, Vol. 1, pg. 312, 1961, Pergamon Press, N.Y.).

It is, accordingly, an object of this invention to provide novel compositions of matter.

It is also an object of this invention to provide compositions adapted for use as multifunctional additives in hydrocarbons, particularly for fuels and oils.

It is also an object of this invention to provide compositions useful as corrosion, oxidation inhibitors and/or dispersants in hydrocarbon lubricating oils.

SUMMARY OF THE INVENTION

It has been discovered that an allylic thiocyanate resulting from the reaction of an alkenyl halide with potassium thiocyanate is, after isomerization to an isothiocyanate, susceptible to derivatization with protoic reactants, particularly upon reaction with: amines, preferably alkylene polyamines: alcohols, preferably polyols; thiols; and, mixtures thereof to yield thiocarbamyl derivatives having activity in hydrocarbons, particularly fuels and lubricating oils.

It is a feature of this discovery that the presence of an allylic carbon-to-carbon double bond in an alkenyl halide makes possible after a displacement reaction with an inorganic thiocyanate salt the isomerization of said alkenyl thiocyanate into an alkenyl isothiocyanate. The isothiocyanate moiety provides the means for: reaction with compounds containing a labile hydrogen such as found in amines, alcohols, and thiols; reaction with substituted benzenes such as an alkyl substituted benzene; and, ring closure reactions such as with thioglycolic acids or esters.

DETAILED DESCRIPTION OF THE INVENTION

The preparation of the allylically unsaturated alkenyl thiocyanate involves a reaction of an alkenyl halide, preferably alkenyl chloride with at least an equal molar proportion of an inorganic thiocyanate salt.

ALKENYL HALIDES

The alkenyl halides for the purpose of this invention are those which are allylically unsaturated with respect to the halide substituent. Such alkenyl halides are commercially available and can readily be demonstrated by the preferred reactant, i.e. polyisobutenyl chloride having a ($\overline{M}_n$) ranging from 700 to 250,000. The invention has application to those alkenyl halides which have broadly a structure

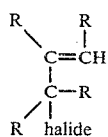

wherein R may be hydrogen or hydrocarbon or substituted hydrocarbon containing from 1 to 20,000 carbons with the restriction that at least one R has at least 6 carbons, preferably from 10 to 150 carbons and optimally from about 60 to about 100 carbons.

Suitable alkenyl substituents are available from olefins, which include butene, isobutene, pentene, decene, dodecene, tetradecene, hexadecene, octadecene, eicosene, and polymers of propylene, butene, isobutene, pentene, decene and the like. In branched alkenyl substituents, particularly branched polyolefins, R may be hydrogen, methyl or a longchain hydrocarbon group. However, the exact structure may not always be ascertained and the various R groups cannot always be precisely defined. The olefins may also contain cycloalkyl and aromatic groups. The most preferred alkenyl halides used in this invention are those in which the alkenyl group contains a total of from 6 to 20,000 carbon atoms; and, at least 10 to 150 and more preferably 60 to 100 for mineral oil systems.

Preferred halogenated olefin polymers for reaction with the thiocyanate salts are from polymers comprising a major molar amount of $C_2$ to $C_5$ monoolefin, e.g., ethylene, propylene, butylene, isobutylene and pentene. The polymers can be homopolymers such as polyisobutylene, as well as copolymers of two or more of such olefins such as copolymers of ethylene and propylene; butylene and isobutylene; propylene and isobutylene; etc. Other copolymers include those in which a minor molar amount of the copolymer monomers, e.g., 1 to 20 mole %, is a $C_4$ to $C_{18}$ nonconjugated diolefin, e.g., a copolymer of isobutylene and butadiene; or a copolymer of ethylene, propylene, and 1,4-hexadiene; etc.

The halogenated olefin polymers will usually have number average molecular weights ($\overline{M}_n$) within the range of 700 and about 250,000; more usually between about 900 and about 10,000. Particularly useful halogenated olefin polymers have ($\overline{M}_n$) within the range of about 1200 and about 5000 with approximately one terminal double bond per polymer chain. An especially valuable starting material for a highly potent dispersant additive are polyalkenes e.g. polyisobutylene, having about 90 carbons.

Especially useful when it is desired that the dispersant additives also possess viscosity index improving properties are 5,000 to 250,000 e.g., 25,000 to 100,000 number average molecular weight polymers. An especially preferred example of such a V.I. improving polymer is a copolymer of about 30 to 85 mole % ethylene, about 15 to 70 mole % $C_3$ to $C_5$ monoalpha-olefin, preferably propylene, and 0 to 20 mole % of a $C_4$ to $C_{14}$ nonconjugated diene.

These ethylene-propylene V.I. improving copolymers or terpolymers are usually prepared by Ziegler-Natta synthesis methods. Some of these copolymers and terpolymers are commercially available such as VISTALON ®, an elastomeric terpolymer of ethylene, propylene and 5-ethylidene norbornene, marketed by Exxon Chemical Co., New York, N.Y. and NORDEL ®, a terpolymer of ethylene, propylene and 1,4-hexadiene marketed by E. I. duPont de Nemours & Co.

SALTS OF THIOCYANIC ACID

Any inorganic salt of thiocyanic acid can be reacted with the allylically unsaturated alkenyl halide e.g. polyisobutenyl chloride, to produce the alkenyl thiocyanates. Sodium thiocyanate, strontium thiocyanate, potassium thiocyanate, and ammonium thiocyanate may be mentioned by way of nonlimiting example. Potassium thiocyanate is the preferred inorganic salt reactant.

PREPARATION OF ALKENYL ISOTHIOCYANATE

The reaction is a two-part reaction wherein the alkenyl thiocyanate is first obtained followed by its isomerization to the alkenyl isothiocyanate.

The reaction between the inorganic salt reactant and the alkenyl chloride reactant can be effected in several ways, such as, for example, by fusing the reactants. Suitably, the reaction can be effected by refluxing a mixture of the polyisobutenyl chloride reactant and an excess of the inorganic salt reactant neat or in a solvent, such as mineral oil, at a temperature of between 0° to 150° C., preferably 50° to 100° C. for between 0.25 and 5 hours.

The isomerization occurs after formation of the thiocyanate in a manner which is believed to be displacement of the halogen substituent, e.g. chloro, by the sulfur of the thiocyanate radical and subsequent reaction of the chloride ion by the cation of the thiocyanate salt, e.g. the potassium. The displacement of the chloro substituent allows for substitution of the sulfur ion followed by a double bond shift as follows:

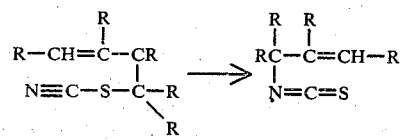

wherein R is as earlier defined.

The resulting products thus include diisobutenyl isothiocyanate, octadecenyl isothiocyanate, polyisobutenyl ($C_{60}$–$C_{100}$) isothiocyanate, poly(ethylene-propylene-1,4-hexadiene) isothiocyanate, poly(ethylene-propylene-2,5-ethylidenenorbornene) isothiocyanate and poly(ethylene-propylene) isothiocyanate.

The isomerization can be facilitated by the presence of from 1 to 3% of a phase transfer agent which includes quaternary ammonium compounds such as tetradodecyl ammonium chloride, cetyl trimethyl ammonium bromide and organic bases such as trialkylamines, e.g. tridecyl amine, tridodecyl amine, trihexylamine and tributylamine and other alkyl amines such as n-hexadecylamine, n-decylamine, dibutylamine and dipropylamine.

REACTIONS OF THE ALKENYL ISOTHIOCYANATES

As earlier discussed, the novel alkenyl isothiocyanates of the invention can be readily derivatized into thiocarbamyl compounds for enhanced additive activity by: reaction with compounds containing a labile hydrogen, preferably amines, alcohols and thiols; reaction with a benzene compound such as alkylated benzenes; and, ring closure with a thio compound such as thioglycolic acid.

A. The Amines

The reaction of the alkenyl isothiocyanate with an amine provides a thiourea derivative e.g. polyisobutenyl isothiocyanate reacted with diethylene triamine can be represented as follows:

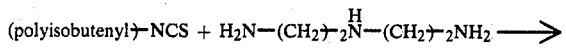

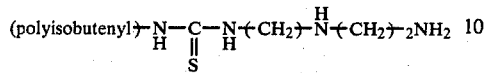

Useful amines are those compounds characterized by a radical having the structural configuration

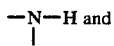

the two remaining valences of the nitrogen valences of the nitrogen atom of the

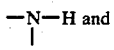

above radical preferably are satisfied by hydrogen, amino, or organic radicals bonded to said nitrogen atom through direct carbon-to-nitrogen linkages. Thus, the compounds from which the nitrogen-containing group may be derived include aliphatic amines, aromatic amines, heterocyclic amines or carbocyclic amines. The amines may be primary or secondary amines and preferably are polyamines such as alkylene amines, arylene amines, cyclic polyamines, and the hydroxy-substituted derivatives of such polyamines.

Thus the useful amines include mono- and polyamines of 2 to 60, e.g. 3 to 20 total carbon atoms and from 1 to 12, e.g. 2 to 6 nitrogen atoms in the molecule. The amine compounds may be hydrocarbyl amines or may include hydroxy groups, alkoxy groups, amide groups or may be cyclic in structure such as imidazolines and the like.

The preferred amines are the alkylene polyamines having the following formulas:

(a) alkylene polyamines

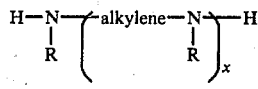

wherein x is an integer of 1 to 10, preferably 2 to 4, R is hydrogen, a hydrocarbon or substantially a hydrocarbon group containing 1 to 7, preferably 1 to 4 carbon atoms and the alkylene radical is a straight or branched chain alkylene radical having up to 7 preferably 2 to 4 carbon atoms;

(b) polyoxyalkylene polyamines (i) $NH_2$—alkylene—$(O$-alkylene$)_{\overline{m}}NH_2$ where m has a value of about 3 to 70 and preferably 10 to 35; and, (ii) R—[alkylene—$(O$-alkylene$)_{\overline{n}}NH_2$]3–6 where n has a value of about 1 to 40 with the proviso that the sum of all the n's is from 3 to 70 and preferably from 6 to 35 and R is a polyvalent saturated hydrocarbon radical of up to 10 carbon atoms having a valence of 3 to 6. The alkylene groups in either formula (i) or (ii) may be straight or branched chains containing about 1 to 7 and preferably about 1 to 4 carbon atoms.

The alkylene polyamines of formula (a) above include, for example, methylene amines, ethylene amines, butylene amines, propylene amines, pentylene amines, hexylene amines, heptylene amines, octylene amines, other polymethylene amines, and the cyclic and higher homologs of these amines such as the piperazines, and the aminoalkyl-substituted piperazines. These amines include, for example, ethylene diamine, triethylene tetramine, propylene diamine, di(heptamethylene) triamine, tripropylene tetramine, tetraethylene pentamine, trimethylene diamine, pentaethylene hexamine di(trimethylene) triamine, 2-heptyl-3-(2-aminopropyl) imidazoline, 4-methylimidazoline, 1,3-bis-(2-aminoethyl) imidazoline, pyrimidine, 1-(2-aminopropyl) piperazine, 1,4-bis-(2-aminoethyl) piperazine, N,N-dimethylaminopropyl amine, N,N-dioctylethyl amine, N-octyl-N'-methylethylene diamine, and 2-methyl-1-(2-aminobutyl) piperazine. Other higher homologs which may be used can be obtained by condensing two or more of the above-mentioned alkylene amines in a known manner.

The ethylene amines which are particularly useful include diethylene triamine, tetraethylene pentamine, octaethylene nonamine, tetrapropylene pentamine, as well as various cyclic polyalkyleneamines. A particularly useful alkylene amine comprises a mixture of ethylene amines prepared by the reaction of ethylene chloride and ammonia which may be characterized as having a composition that corresponds to that of tetraethylene pentamine.

Alkylene amines having one or more hydroxyalkyl substituents on the nitrogen atoms may be used. These hydroxyalkyl-substituted alkylene amines are preferably compounds wherein the alkyl group is a lower alkyl group, i.e. having less than about 6 carbon atoms and include, for example, N-(2-hydroxyethyl) ethylene diamine, N,N'-bis(2-hydroxyethyl) ethylene diamine, 1-(2-hydroxyethyl) piperazine, monohydroxypropyl-substituted diethylene triamine, 1,4-bis(2-hydroxypropyl)-piperazine, dihydroxy-propyl-substituted tetraethylene pentamine, N-(3-hydroxy-propyl) tetramethylene diamine, 2-heptadecyl-1-(2-hydroxyethyl) imidazole, etc.

The polyoxyalkylene polyamines of formula (b) above, e.g. polyoxyalkylene diamines and polyoxyalkylene triamines, may have average molecular weights ranging from about 200 to about 4000 and preferably from about 400 to 2000. The preferred polyoxyalkylene polyamines for purposes of this invention include the polyoxyethylene and polyoxypropylene diamines and the polyoxypropylene triamines having average molecular weights ranging from about 200 to 2000. The polyoxyalkylene polyamines are commercially available and may be obtained, for example, from the Jefferson Chemical Company, Inc. under the trade name "Jeffamines D-230, D-400, D-1000, D-2000, T-403," etc.

Other useful amine compounds include: alicyclic diamines such as 1,4-bis-(aminoethyl) cyclohexane, and heterocyclic nitrogen compounds such as imidazolines and N-aminoalkyl piperazines of the general formula:

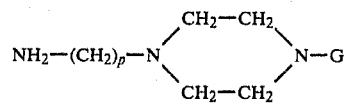

wherein G is independently selected from the group consisting of hydrogen and Ω aminoalkylene radicals of from 1 to 3 carbon atoms; and p is an integer of from 1 to 4. Nonlimiting examples of such amines include 2-pentadecyl imidazoline; N-(2-aminoethyl) piperazine; N-(3-aminopropyl) piperazine; and N,N'-di-(2-aminoethyl)piperazine.

B. The Alcohols a. Monohydric Alcohols

Useful monohydric alcohols can be characterized by the formula R'OH wherein R' is an alkyl or heteroalkyl group containing from 1 to 24, preferably 1 to 12, carbons such as methyl, ethyl, propyl, butyl, hexyl, octyl, decyl, lauryl, stearyl and mixtures thereof; and heteroatom-containing aliphatic radicals such as $CH_3O(CH_2CH_2O)_nCH_2CH_2-$, $CH_3S(CH_2CH_2S)_n-CH_2CH_2-$, $(CH_3)_2N(CH_2CH_2NCH_3)_nCH_2CH_2-$; etc., where $n=1-10$, and 1-aza-3,7-dioxabicyclo(3.3.0)oct-5-methanol. The resulting esters when used as additive components for mineral lubricating oils and fuels provide improved properties of antiwear, anticorrosion, friction modification or lubricity modification.

b. Polyhydric Alcohols

The polyhydric alcohols used in esterifying the isothiocyano compounds can have a total of 2 to 100 carbon atoms and can be represented by the formula:

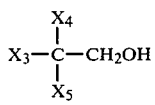

wherein: $X_3$ is hydrogen, $C_1$ to $C_5$ alkyl, hydroxyl, hydroxyalkyl $HO(CH_2)_n$ wherein n is 1–10, hydroxyalkoxy $HO(CH_2CH_2O)_n-$, wherein n is 1–40, hydroxyalkylthio $HOCH_2CH_2S(CH_2CH_2S)_n-$, wherein n is 1 to 10; and hydroxyalkylamino $HO(CH_2CH_2NCH_3)_n-$, wherein n is 1 to 10; and $X_4$ and $X_5$ may be the same or different and represent hydrogen, $C_1$ to $C_5$ alkyl and $C_1$ to $C_5$ hydroxyalkyl groups and their ester, ether, acetal or ketal derivatives. Examples of useful acetals and ketals include mono- and bis-formals of pentaerythritol; mono- and bis-acetal and benzal analogs of pentaerythritol; and the cyclic formal and acetal of $HO(CH_2CH_2O)_nH$ wherein n is 4–8.

An especially preferred class of polyhydric alcohols are typified by pentaerythritol, dipentaerythritol, tripentaerythritol, polypentaerythritols, sorbitol, mannitol, cyclohexaamylose, cycloheptaamylose and related polyhydric alcohols such as these prepared via the aldol condensation of formaldehyde with ketones such as acetone, and cyclohexanone, e.g. 2,2,6,6-tetramethylol-1-cyclohexanol.

The esterification process is carried out according to conventional procedures by reacting from 0.25 to 1 moles of the alkenyl isothiocyanate to a mole of alkanol preferably the polyol at a temperature of from 50° C. to 200° C. until the reaction is complete by infrared monitoring of the reaction products until maximum C-O absorption is determined.

c. The Thiols

In the preparation of the dithiocarbamic ester derivatives which conform to the formula

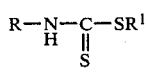

R is as earlier defined and R' represents a hydrocarbyl (both substituted and nonsubstituted) having from 2 to 100 carbons. Thus the hydrocarbon thiol reactant contains between 2 and 100 carbon atoms with an attached thiol or alkali or alkaline earth metal thiolate group. Suitable thiols include but are not limited to n-butyl mercaptan, isobutyl mercaptan, t-butyl mercaptan, hexyl mercaptans, octyl mercaptans, diisobutenyl mercaptan, decyl mercaptans, dodecyl mercaptans, cetyl mercaptans, cyclohexyl mercaptan, benzyl mercaptan, thiophenol and longer chain alkyl mercaptans derived from propene polymers and isobutylene polymers. It is understood that the above thiols may also be used as their alkali or alkaline earth metal salts, i.e. thiolates.

Other suitable reactants include monothio acids and dithio acids such as thioacetic, thiobenzoic, dithioacetic, dithiopropionic, and dithiobenzoic acid; useful thiophosphoric and esters include dialkyl dithiophosphoric anc diaryl dithiophosphoric acid. The corresponding salts of the above acids, i.e. thioates, are equally useful.

Other suitable reactants containing a metal thiolate group are dithiocarbamates such as sodium diethyl dithiocarbamate, sodium dibutyl dithiocarbamate; xanthates such as sodium ethyl xanthate and sodium butyl xanthate; trithiocarbonates, such as sodium t-butyl trithiocarbonate and sodium t-octyl trithiocarbonate.

Other thiol reactants are mercapto substituted azoles and azolines. Representative azoles include oxadiazoles, isoxazoles, isothiazoles, oxazoles, diazoles, triazoles, thiazoles, imidazoles, benzoxazole, benzimidazoles, etc. Representative azolines include thiazolines, oxazolines and imidazolines. Thus included are 2-mercapto-thiazole, 2-mercapto-oxazole, 2-mercapto-imidazole, 2-mercapto-thiazoline, 2-mercapto-oxazoline, 2-mercapto-imidazoline, 2-mercapto-benzothiazole, 2-mercapto-benzoxazole 2-mercapto-benzimidazole 2,5 dimercapto 1,3,4-thia-diazole and 3,5-dimercapto 1,2,4 thiadiazole. Equally useful are the alkali or alkaline earth metal thiolate salts of the azoles or azolines.

USE OF THE ADDITIVE IN HYDROCARBON COMPOSITIONS

The isothiocyanate and thiocarbamyl reaction products of this invention can be incorporated into a wide variety of hydrocarbon compositions. They can be used in lubricating oil compositions, such as automotive crankcase lubricating oils, automatic transmission fluids, etc., in concentrations generally within the range of about 0.01 to 20 wt.%, e.g. 0.1 to 10 wt.%, preferably 0.3 to 3.0 wt.%, of the total composition. The lubricants to which the products of the invention can be added include not only hydrocarbon oils from petroleum, but also include synthetic lubricating oils such as polyethylene oils; alkyl esters of dicarboxylic acid; complex esters of dicarboxylic acid, polyglycol and alcohol; alkyl esters of carbonic or phosphoric acids; polysilicones; fluorohydrocarbon oils; mixtures of mineral lubricating oil and synthetic oils in any proportion, etc.

When the products of this invention are used in petroleum fuels such as gasoline, kerosene, diesel fuels, No. 2 fuel oil and other middle distillates to provide antirust properties, a concentration of the additive in the fuel of from 4 to 20 parts per million based on the weight of the total composition, will usually be employed.

The additives of the invention may be conveniently dispensed as an additive concentrate of from 2 wt.% to 100 wt.% with the balance conventionally a mineral lubricating oil e.g. up to 90 wt.%, with or without other additives being present.

In the above compositions or concentrates, other conventional additives may also be present including dyes, pour point depressants, antiwear agents such as $P_2S_5$-treated terpene or zinc dialkyl dithiophosphates of 3 to 8 carbon atoms in each alkyl group, antioxidants such as N-phenyl-αnaphthylamine, tert-octylphenol sulfide, 4,4'-methylene bis (2,6-di-tert-butyl phenol), viscosity improvers such as ethylene-propylene copolymers, polymethacrylates, polyisobutylene, alkyl fumarate-vinyl acetate copolymers and the like, deemulsifiers such as polysiloxanes, ethoxylated polymers and the like.

The invention will be further understood by reference to the following examples, which include preferred embodiments of the invention.

EXAMPLE 1

1000 grams of chlorinated polyisobutylene (3.3 wt.% chloride) having a number average molecular weight ($\overline{M}_n$) of about 100 was stirred with 99.2 grams of KSCN under a nitrogen blanket for 3 hours at 150° C. An additional 20 grams of KSCN was added and thereafter the reactant mixture was heated for 7 hours at 150° C. The reactant mixture was cooled to room temperature, diluted with an equal volume of hexane and filtered using a filter aid. The hexane was then evaporated from the solution leaving the product polyisobutenyl isothiocyanate which analyzed for 0.41 wt.% chlorine, 0.62 wt.% nitrogen and 1.36 wt.% sulfur. The $\overline{M}_n$ was 1036, the ratio of infrared absorption peaks at $$\frac{2090 \text{ cm}^{-1} \text{ (NCS)}}{1240 \text{ cm}^{-1} \text{ (isobutylene)}} \text{ was } 0.57.$$

EXAMPLES 2 and 3

The chlorinated polyisobutylene of Example 1 was further chlorinated to a level of 9.2 wt.% and 16.8 wt.% in two samples 2 and 3 by dissolving 500 grams each of said polyisobutylene in 500 ml of hexane and bubbling chlorine through said solutions until said desired levels of chlorine were each reached.

50 grams of each respective sample was reacted with powdered KSCN by heating with stirring for 2.5 hours at 150° C. After dilution, filtration and isolation according to the procedure of Ex. 1 the respective products were analyzed. The data obtained was:

|  | Sample 2 | Sample 3 |
|---|---|---|
| % chlorine of chloropolyisobutylene | 9.2 | 16.8 |
| gr. KSCN added | 15 | 27.6 |
| % Cl in product | 3.85 | 4.08 |
| % N in product | 1.28 | 2.32 |
| % S in product | 2.45 | 2.62 |
| IR 2090 cm$^{-1}$ / 1240 cm$^{-1}$ | 0.94 | 0.22 |

EXAMPLE 4

The product polyisobutylene isothiocyanates of Example 1 was reacted with 1 gram of diethylene triamine by diluting 10 grams of said product with 10 grams of S150N mineral oil and heating with the diethylene triamine (DETA) for 3 to 4 hours at 120° C. The molar reactant ratio of alkylene polyamine to polyisobutylene isothiocyanate was estimated at one molar equivalent of the latter for each mole of the former.

The resulting thiourea product, i.e.

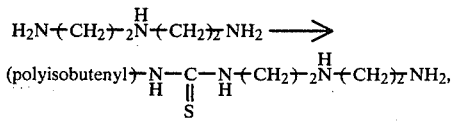

$$(\text{polyisobutenyl})\!-\!N\!=\!C\!=\!S +$$

$$H_2N\!-\!(CH_2)_{\overline{2}}\overset{H}{N}\!-\!(CH_2)_{\overline{2}}NH_2 \longrightarrow$$

$$(\text{polyisobutenyl})\!-\!\underset{H}{N}\!-\!\underset{\underset{S}{\|}}{C}\!-\!\underset{H}{N}\!-\!(CH_2)_{\overline{2}}\overset{H}{N}\!-\!(CH_2)_{\overline{2}}NH_2,$$

analyzed for 2.12 wt.% N.

EXAMPLE 5

The procedure of Ex. 4 was followed except that the product of Ex. 2 was reacted with 2.7 grams of DETA. The resultant thiourea product analyzed for 4.5 wt.% N.

EXAMPLE 6

The procedure of Ex. 4 was followed except that the product of Ex. 3 was reacted with 4.9 grams of DETA. The resultant thiourea product analyzed for 4.3 wt.% N.

EXAMPLE 7

A 2000 gram sample of Indopol 300, a polyisobutylene commercially available from Amoco Chemicals Corp. of Chicago, Ill. which is believed to have a $\overline{M}_n$ of about 1300, was chlorinated by bubbling chlorine through a hexane solution of each containing 1500 grams of hexane. The added $Cl_2$ was 53 grams resulting in polyisobutenyl chloride which analyzed for 2.97 wt.% Cl.

The 200 grams of the polyisobutenyl chloride was admixed with a solution of 15.5 grams of KSCN dissolved in 6.5 grams of water. After heating at 150° C. for 10 hours, the reactants were filtered and polyisobutenyl ($\overline{M}n$ of 1300) isothiocyanate was recovered.

50 grams of the recovered product was dissolved in 50 grams of Solvent 150 N mineral oil and thereafter heated at 140° C. for 3 hours with a commercial alkylene polyamine which approximated tetraethylene pentamine (TEPA). After cooling the product was washed with methanol.

EXAMPLE 8

The procedure of Example 7 was followed except that:

(a) 103 grams of chlorine were added resulting in a polyisobutenyl ($M_n$ of 1300) chloride containing 6 wt.% chlorine;

(b) 29.3 grams of KSCN dissolved in 13 grams of $H_2O$ was added; and, (c) 19 grams of TEPA was added.

EXAMPLE 9

10 grams of the product polyisobutenyl isothiocyanate of Sample 3 (analyzed for 2.3 wt.% N) and 2.6 wt.% S) was dissolved in 10 grams of Solvent 150 N mineral oil and reacted with 2 grams of tetraethylene pentamine at 140° C. for 3¾ hours. The resulting product was dialysed in hexane and recovered by precipitating from methanol.

EXAMPLE 10

To evaluate in part the utility of the products of the invention, a number of samples were subjected to the Sludge Inhibition Bench (SIB) Test and to the Varnish Inhibition Bench (VIB) Test.

The Sludge Inhibition Bench Test is conducted in the following manner. The aforesaid used crankcase oil which is milky brown in color, is freed of sludge by centrifuging for ½ hour at about 39,000 gravities (gs.). The resulting clear, bright red supernatant oil is then decanted from the insoluble sludge particles thereby separated out. However, the supernatant oil still contains oil-soluble sludge precursors which on heating under the conditions employed by this test will tend to form additional oil-insoluble deposits of sludge. The sludge inhibiting properties of the additives being tested are determined by adding to portions of the supernatant used oil, a small amount, such as 0.5, 1.0 or 1.5 wt.%, on an active ingredient basis, of the particular additive being tested. Ten grams of each blend being tested is placed in a stainless steel centrifuge tube and is heated at 138° C. for 16 hours in the presence of air. Following the heating, the tube containing the oil being tested is cooled and then centrifuged for 30 minutes at about 39,000 gs. Any deposits of new sludge that form in this step are separated from the oil by decanting the supernatant oil and then carefully washing the sludge deposits with 15 ml. of pentane to remove all remaining oil from the sludge. Then the weight of the new solid sludge that has been formed in the test, in milligrams, is determined by drying the residue and weighing it. The results are reported as milligrams of sludge per 10 grams of oil, thus measuring differences as small as 1 part per 10,000. The less new sludge formed the more effective is the additive as a sludge dispersant. In other words, if the additive is effective, it will hold at least a portion of the new sludge that forms on heating and oxidation, stably suspended in the oil so it does not precipitate down during the centrifuging.

In the Varnish Inhibition Bench (VIB) Test, each test sample consisted of 10 grams of lubricating oil containing 0.07 of a gram of the additive concentrate (50% active) which results in a total of 0.35 wt.% additive present in the test sample. The test oil to which the additive is admixed was 9.93 grams of a commercial lubricating oil obtained from a taxi after 2,000 miles of driving with said lubricating oil. Each ten gram sample was heat soaked overnight at about 140° C. and thereafter centrifuged to remove the sludge. The supernatant fluid of each sample was subjected to heat cycling from about 100° C. to room temperature over a period of 3.5 hours at a frequency of about 2 cycles per minute. During the heating phase, the gas containing a mixture of about 0.7 volume percent $SO_2$, 1.4 volume percent NO and balance air was bubbled through the test samples and during the cooling phase water vapor was bubbled through the test samples. At the end of the test period, which testing cycle can be repeated as necessary to determine the inhibiting effect of any additive, the wall surfaces of the test flasks in which the samples were contained are visually evaluated. Flasks in which the samples were contained are visually evaluated as to the varnish inhibition. The amount of varnish imposed on the walls is rated at values of from 1 to 7 with the higher number being the greater amount of varnish. It has been found that this test correlates with the varnish results obtained as a consequence of carrying out an MS-VC engine test.

Using the above-described tests, the dispersant action of thiourea additive of the present invention was compared with the dispersing power of one commercial dispersant referred to as PIBSA/TEPA. The PIBSA/TEPA was prepared by reaction of 1 mole of tetraethylene pentamine with about 2 moles of polyisobutenyl succinic anhydride obtained from polyisobutylene of about 1000 number average molecular weight. The PIBSA/TEPA dispersant was used as an additive concentrate containing about 50 wt.% PIBSA/TEPA in 50 wt.% mineral lubricating oil.

The test results are given in the Table below.

TABLE I

| | Sludge Inhibition Bench Test Results | |
|---|---|---|
| Additive | Mg Sludge/10g Oil at 0.7 wt. % | VIB Test Rating |
| Blank | 28.5 | — |
| Example 2 | 26.5 | — |
| Example 3 | 22.8 | — |
| Example 4 | 19.4 | — |
| Blank | 28.3 | — |
| Example 7 | 23.8 | — |
| Blank | 29.0 | 11 |
| Example 9 | 7.8 | 5 |
| PIBSA/TEPA | 10.9 | 7 |

From the experimental data, it appears certain that the products of the invention provide sludge dispersant activity to lubricating oils and for the product of Example 9 sludge dispersant and varnish inhibition activities are imparted to the oil superior to a commercially available lubricating oil additive.

The data and experience in carrying out the Examples indicates that the molar reaction rate of the polyisobutylene isothiocyanate should preferably range from 1.5 to 3, optimally about 2 molar equivalents of isothiocyanate per mole of alkylene polyamine.

The thiourea products of the Examples also provide varnish-inhibiting activity to lubricating oils.

Earlier in the text reference was made to the fact that the allylically unsaturated alkenyl isothiocyanate could react with substituted benzenes and undergo ring closure with thio glycolic materials.

It is part of this invention that the aforesaid alkenyl isothiocyanates could react with benzene compounds as follows:

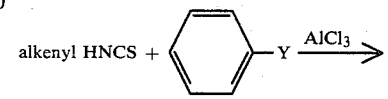

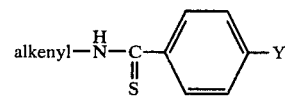

wherein Y is a hydrocarbyl group containing from 1 to 100 carbons. Representative benzene compounds include toluene, phenol, biphenyl, octyl benzene, nitrobenzene, etc.

The ring closure reaction is represented as follows:

-continued

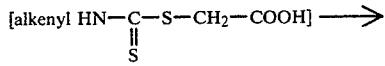

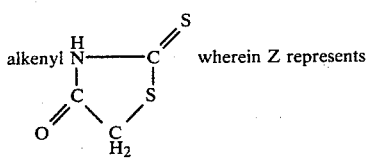 wherein Z represents hydrogen or an alkyl group containing from 1 to 5 carbons. Representative thioglycolic compounds include thioglycolic acid, methyl thioglycolate, ethyl thioglycolate, etc.

It is to be understood that the Examples present in the foregoing specification are merely illustrative of this invention and are not intended to limit it in any manner; nor is the invention to be limited by any theory regarding its operability. The scope of the invention is to be determined by the appended claims.

What is claimed is:

1. A composition comprising a lubricating oil containing 0.01 to 20 weight percent of a thiocarbamyl derivative of an allylicly unsaturated polyisobutenyl isothiocyanate, the polyisobutenyl having a number average molecular weight of 1,200 to 5,000, said derivative being formed by reaction of said polyisobutenyl isothiocyanate with an alkylene polyamine having 2 to 60 carbon atoms.

2. The composition of claim 1 wherein said alkylene polyamine is an ethylene polyamine having 2 to 4 ethylene groups.

* * * * *